US008958862B2

(12) United States Patent
Hetke et al.

(10) Patent No.: US 8,958,862 B2
(45) Date of Patent: Feb. 17, 2015

(54) IMPLANTABLE DEVICE INCLUDING A RESORBABLE CARRIER

(75) Inventors: Jamille F. Hetke, Brooklyn, MI (US); Daryl R. Kipke, Dexter, MI (US); Rio J. Vetter, Ypsilanti, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 1436 days.

(21) Appl. No.: 12/253,813

(22) Filed: Oct. 17, 2008

(65) Prior Publication Data

US 2009/0132042 A1 May 21, 2009

Related U.S. Application Data

(60) Provisional application No. 60/980,659, filed on Oct. 17, 2007.

(51) Int. Cl.
*A61B 5/0478* (2006.01)
*A61N 1/05* (2006.01)
*A61B 5/04* (2006.01)

(52) U.S. Cl.
CPC ............. *A61N 1/05* (2013.01); *A61B 5/04001* (2013.01); *A61B 2562/0209* (2013.01); *A61B 2562/028* (2013.01); *A61B 2562/046* (2013.01); *A61N 1/0551* (2013.01)
USPC ............ 600/378; 600/377; 600/544; 607/116

(58) Field of Classification Search
CPC ............. A61B 5/04001; A61B 5/0476; A61B 5/0478; A61B 5/40; A61B 5/4058; A61B 5/4064; A61B 5/4076–5/4094; A61B 5/6847; A61B 5/6868; A61B 2017/00004; A61B 2017/00831; A61B 2562/0209; A61B 2562/043; A61B 2562/16; A61B 2562/164; A61B 2562/166; A61N 1/04; A61N 1/05; A61N 1/0526; A61N 1/0529; A61N 1/0531; A61N 1/0534
USPC .......... 600/373, 377, 378; 607/115, 116, 118; 606/129
See application file for complete search history.

(56) References Cited

U.S. PATENT DOCUMENTS 3,847,687 A  11/1974  Davidsohn et al.
3,921,916 A  11/1975  Bassous
(Continued)

FOREIGN PATENT DOCUMENTS

CA  PCT/CA00/00942  2/2001
EP  PCT/EP00/10775  5/2002
(Continued)

OTHER PUBLICATIONS

Seymour, John P., Kipke, Daryl R. "Neural probe design for reduced tissue encapsulation in CNS" 28 (2007) 3594-3607, Apr. 5, 2007.
(Continued)

*Primary Examiner* — Lee S Cohen
*Assistant Examiner* — Erin M Cardinal
(74) *Attorney, Agent, or Firm* — Michael F. Scalise

(57) ABSTRACT

An implantable device for body tissue, including an electrical subsystem that flexes within and interfaces with body tissue and a carrier that operates in the following two modes: provides structural support for the electrical subsystem during implantation of the device in body tissue and allows flexing of the electrical subsystem after implantation of the device in body tissue. The implantable device is preferably designed to be implanted into the brain, spinal cord, peripheral nerve, muscle, or any other suitable anatomical location. The implantable device, however, may be alternatively used in any suitable environment and for any suitable reason.

39 Claims, 3 Drawing Sheets

(56) References Cited

U.S. PATENT DOCUMENTS

| | | | |
|---|---|---|---|
| 4,141,365 A | 2/1979 | Fischell et al. | |
| 4,166,469 A | 9/1979 | Littleford | |
| 4,306,562 A | 12/1981 | Osborne | |
| 4,455,192 A | 6/1984 | Tamai | |
| 4,461,304 A | 7/1984 | Kuperstein | |
| 4,465,482 A | 8/1984 | Tittel | |
| 4,762,135 A | 8/1988 | van der Puije | |
| 4,886,065 A | 12/1989 | Collins | |
| 4,904,237 A | 2/1990 | Janese | |
| 5,108,819 A | 4/1992 | Heller et al. | |
| 5,180,376 A | 1/1993 | Fischell | |
| 5,207,709 A | 5/1993 | Picha | |
| 5,215,088 A | 6/1993 | Normann et al. | |
| 5,263,977 A * | 11/1993 | Adams et al. | 607/122 |
| 5,308,442 A | 5/1994 | Taub et al. | |
| 5,322,064 A | 6/1994 | Lundquist | |
| 5,385,635 A | 1/1995 | O'Neill | |
| 5,390,671 A | 2/1995 | Lord | |
| 5,409,469 A | 4/1995 | Schaerf | |
| 5,496,360 A * | 3/1996 | Hoffmann et al. | 607/120 |
| 5,515,848 A | 5/1996 | Corbett, III et al. | |
| 5,524,338 A | 6/1996 | Martyniuk et al. | |
| 5,573,520 A | 11/1996 | Schwartz et al. | |
| 5,585,827 A | 12/1996 | Murakami | |
| 5,588,597 A | 12/1996 | Reinecke et al. | |
| 5,653,742 A * | 8/1997 | Parker et al. | 607/137 |
| 5,716,391 A * | 2/1998 | Grandjean | 607/127 |
| 5,720,099 A | 2/1998 | Parker et al. | |
| 5,744,958 A | 4/1998 | Werne | |
| 5,800,535 A | 9/1998 | Howard, III | |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |
| 6,016,449 A | 1/2000 | Fischell et al. | |
| 6,044,304 A | 3/2000 | Baudino | |
| 6,091,979 A * | 7/2000 | Madsen | 600/377 |
| 6,119,044 A * | 9/2000 | Kuzma | 607/137 |
| 6,132,456 A | 10/2000 | Sommer et al. | |
| 6,181,569 B1 | 1/2001 | Chakravorty | |
| 6,205,361 B1 | 3/2001 | Kuzma et al. | |
| 6,228,111 B1 * | 5/2001 | Tormala et al. | 623/1.38 |
| 6,296,630 B1 * | 10/2001 | Altman et al. | 604/508 |
| 6,324,433 B1 | 11/2001 | Errico | |
| 6,325,797 B1 | 12/2001 | Stewart et al. | |
| 6,374,143 B1 | 4/2002 | Berrang et al. | |
| 6,430,443 B1 | 8/2002 | Karell | |
| 6,600,231 B2 | 7/2003 | Tominaga | |
| 6,618,623 B1 | 9/2003 | Pless et al. | |
| 6,829,498 B2 | 12/2004 | ***Rousche et al. | |
| 6,834,200 B2 | 12/2004 | Moxon et al. | |
| 6,878,643 B2 | 4/2005 | Krulevitch et al. | |
| 7,004,948 B1 | 2/2006 | Pianca et al. | |
| 7,006,859 B1 | 2/2006 | Osorio et al. | |
| 7,010,356 B2 | 3/2006 | Jog et al. | |
| 7,011,680 B2 | 3/2006 | Alt | |
| 7,089,059 B1 | 8/2006 | Pless | |
| 7,181,288 B1 | 2/2007 | Rezai et al. | |
| 7,343,205 B1 | 3/2008 | Pianca et al. | |
| 7,548,775 B2 | 6/2009 | Kipke et al. | |
| 7,871,707 B2 | 1/2011 | Laude et al. | |
| 7,914,842 B1 | 3/2011 | Greenberg et al. | |
| 7,941,202 B2 | 5/2011 | Hetke et al. | |
| 8,731,673 B2 * | 5/2014 | Vetter et al. | 607/45 |
| 2001/0049499 A1 | 12/2001 | Lui et al. | |
| 2002/0052610 A1 | 5/2002 | Skakoon et al. | |
| 2002/0183817 A1 | 12/2002 | Van Venrooij et al. | |
| 2002/0198446 A1 | 12/2002 | Hill et al. | |
| 2003/0093104 A1 * | 5/2003 | Bonner et al. | 606/185 |
| 2003/0093129 A1 | 5/2003 | Nicolelis et al. | |
| 2003/0100823 A1 | 5/2003 | Kipke | |
| 2003/0114906 A1 | 6/2003 | Booker et al. | |
| 2003/0187461 A1 | 10/2003 | Chin | |
| 2004/0006264 A1 | 1/2004 | Mojarradi et al. | |
| 2004/0102828 A1 | 5/2004 | Lowry et al. | |
| 2004/0106169 A1 | 6/2004 | Evans | |
| 2004/0122501 A1 * | 6/2004 | Dadd et al. | 607/137 |
| 2004/0199235 A1 | 10/2004 | Younis | |
| 2005/0004627 A1 | 1/2005 | Gibson et al. | |
| 2005/0021116 A1 | 1/2005 | He et al. | |
| 2005/0021117 A1 | 1/2005 | He et al. | |
| 2005/0137647 A1 | 6/2005 | Wallace et al. | |
| 2005/0222647 A1 | 10/2005 | Wahlstrand et al. | |
| 2006/0122677 A1 | 6/2006 | Vardiman | |
| 2006/0173263 A1 * | 8/2006 | He et al. | 600/378 |
| 2006/0247749 A1 | 11/2006 | Colvin | |
| 2006/0258951 A1 | 11/2006 | Bleich et al. | |
| 2006/0276866 A1 | 12/2006 | McCreery | |
| 2006/0282014 A1 | 12/2006 | Kipke et al. | |
| 2007/0073130 A1 | 3/2007 | Finch et al. | |
| 2007/0123765 A1 | 5/2007 | Hetke et al. | |
| 2007/0135885 A1 | 6/2007 | Risi | |
| 2008/0132970 A1 * | 6/2008 | Barolat | 607/46 |
| 2008/0208283 A1 | 8/2008 | Vetter et al. | |
| 2008/0255439 A1 | 10/2008 | Tang et al. | |
| 2008/0262584 A1 | 10/2008 | Bottomley et al. | |
| 2009/0099441 A1 * | 4/2009 | Giszter et al. | 600/377 |
| 2009/0099555 A1 | 4/2009 | Viohl et al. | |
| 2009/0102068 A1 | 4/2009 | Pellinen et al. | |
| 2009/0118806 A1 | 5/2009 | Vetter et al. | |
| 2009/0149934 A1 | 6/2009 | Ameri et al. | |
| 2009/0171421 A1 | 7/2009 | Atalar et al. | |
| 2009/0187196 A1 | 7/2009 | Vetter et al. | |
| 2009/0234426 A1 | 9/2009 | Pellinen et al. | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0145216 A1 | 6/2010 | He et al. | |
| 2010/0145422 A1 | 6/2010 | Seymour et al. | |
| 2011/0093052 A1 | 4/2011 | Anderson et al. | |
| 2011/0154655 A1 | 6/2011 | Hetke et al. | |

FOREIGN PATENT DOCUMENTS

| | | |
|---|---|---|
| UA | PCT/US2004/035030 | 5/2005 |
| WO | 0241666 | 5/2002 |
| WO | 2006138358 A | 12/2006 |
| WO | 2007042999 A | 4/2007 |
| WO | 2007089738 A | 8/2007 |
| WO | 2008011721 A | 1/2008 |
| WO | 2008038208 A | 4/2008 |
| WO | 2008072125 A | 6/2008 |
| WO | 2008109298 A | 9/2008 |
| WO | 2009052423 A | 4/2009 |
| WO | 2009052425 A | 4/2009 |
| WO | 2010057095 A | 5/2010 |
| WO | 2011/010257 | 1/2011 |
| WO | 2011046665 A | 4/2011 |

OTHER PUBLICATIONS

Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009.

Kaplan, et al., "A Novel Fabrication Method of Capillary Tubes on Quartz for Chemical Analysis Applications" IEEE Proceedings, Micro Electro Mechanical Systems, Jan. 25-28, 1994.

Lin, et al., "Silicon Processed Microneedles" The 7th International Conference on Solid State Sensors and Acutators; Jun. 7-10, 1993.

U.S. Appl. No. 12/986,081, Hetke.

Application No. PCT/IB06/53700, International Search Report mailed Nov. 21, 2008.

Application No. PCT/IB10/53250, International Search Report mailed Oct. 4, 2010.

Application No. PCT/US04/35030, International Search Report mailed Feb. 21, 2005.

(56) References Cited

OTHER PUBLICATIONS

Application No. PCT/US06/23139, International Search Report mailed Aug. 2, 2007.
Application No. PCT/US07/02465, International Search Report mailed Feb. 13, 2008.
Application No. PCT/US08/55025, International Search Report and Written Opinion mailed Oct. 27, 2008.
Application No. PCT/US08/80364, International Search Report and Written Opinion mailed Dec. 16, 2008.
Application No. PCT/US08/80366, International Search Report and Written Opinion mailed Dec. 10, 2008.
Application No. PCT/US09/64591, International Search Report and Written Opinion mailed Jul. 21, 2010.
Application No. PCT/US10/44167, International Search Report and Written Opinion mailed Sep. 27, 2010.
Lin et al., "Silicon Processed Microneedles," IEEE J. Micro. Electro. Mech. Sys, vol. 8, No. 1 (1999) 78-84 (7 pages).

* cited by examiner

US 8,958,862 B2

IMPLANTABLE DEVICE INCLUDING A RESORBABLE CARRIER

CROSS-REFERENCE TO RELATED APPLICATIONS

This application claims the benefit of U.S. Provisional Application No. 60/980,659 filed 17 Oct. 2007 and entitled "Carrier for an Implantable Device System", which is hereby incorporated in its entirety by this reference.

This application is related to US Publication Number 2008/0208283 published on 28 Aug. 2008 and entitled "Neural Interface System", which issued as U.S. Pat. No. 8,731,673 on 20 May 2014, and which is incorporated in its entirety by this reference.

TECHNICAL FIELD

This invention relates generally to the implantable device field, and more specifically to an implantable device including a resorbable carrier.

BACKGROUND

Conventional microfabricated electrode arrays by themselves are often not mechanically robust enough to be inserted into body tissue. Therefore, they must be coupled to a carrier that is strong enough to resist buckling while being inserted into the tissue. Conventional carriers typically remain implanted with the microfabricated electrode arrays, potentially reducing the ability of the microfabricated electrode arrays to move freely in the tissue. Thus, there is a need for an improved carrier that increases the ability of the microfabricated electrode arrays to move freely. This invention provides such an improved and useful carrier.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1A:
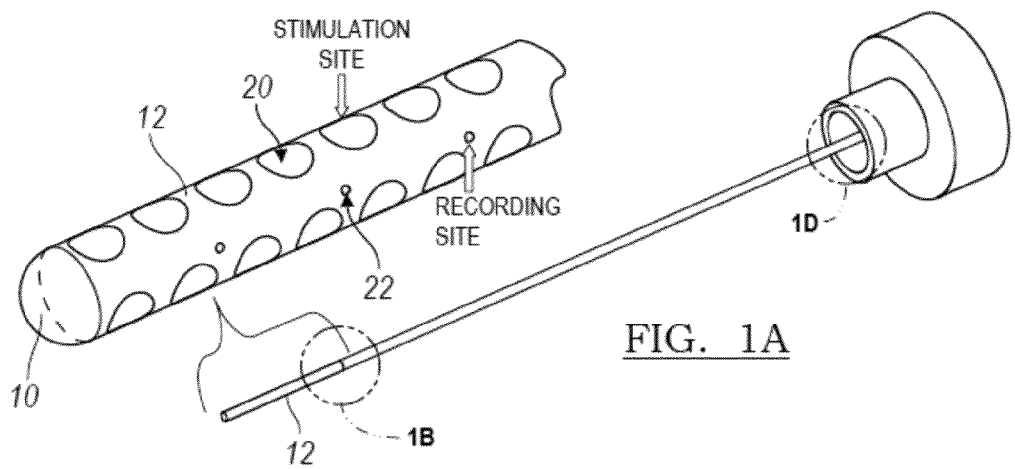
FIG. 1A is a representation of the device of the preferred embodiments of the invention.
Figure 1B:
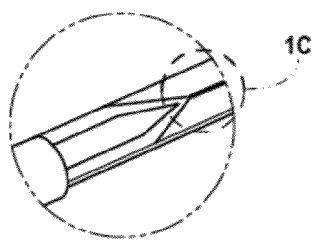
FIGS. 1B-1D are detailed views of FIG. 1A, showing a connector, a more detailed view of the connector, and a proximal end of the system, respectively.
Figure 1C:
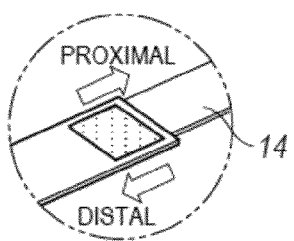
Figure 1D:
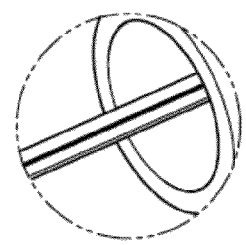
Figure 2:
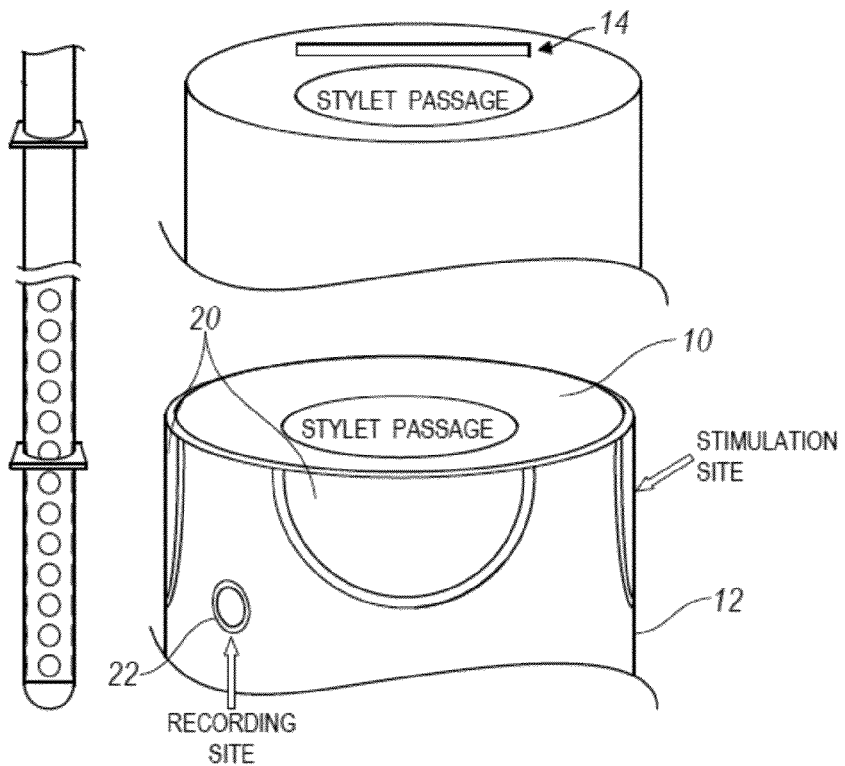
FIG. 2 is a representation of the device of FIG. 1, shown with two cross-sectional views.

As shown in FIGS. 1 and 2, the implantable device of the preferred embodiments includes a carrier 10 and an electrical subsystem 12 coupled to the carrier 10. The carrier 10 functions to facilitate the insertion of the electrical subsystem 12 and is adapted to allow the electrical subsystem 12 to move freely in the tissue. The implantable device is preferably designed to be implanted into the brain, spinal cord, peripheral nerve, muscle, or any other suitable anatomical location. The implantable device, however, may be alternatively used in any suitable environment and for any suitable reason.

The carrier 10 functions to facilitate the insertion of the electrical subsystem 12 and is adapted to allow the electrical subsystem 12 to move freely in the tissue or other substances. The electrical subsystem 12 is preferably attached to the carrier 10 such that the carrier functions to provide structural support. The carrier may include a sharpened end adapted to penetrate the tissue and aid in the insertion of the carrier and electrical subsystems into the tissue. The carrier 10 may also include alignment and or fixation features to facilitate positioning and stabilizing the electrical subsystem 12 in the tissue.

The carrier 10 of the preferred embodiments is resorbable into tissue after a period of time. Upon resorption of the carrier 10, the electrical subsystem 12 supported by the carrier will be left to float freely in the brain or other suitable tissue or material. The resorbable carrier is preferably made of a material that demonstrates at least one of the following characteristics: minimal foreign body reaction, biocompatibility, biodegradability, long-term mechanical and chemical stability, sterilizability, and sufficient porosity. The material is preferably adapted to undergo a controlled action and reaction to the surrounding tissue, a controlled chemical breakdown and resorption, replacement by regenerating tissue, stimulation of regeneration of living tissues, or any combination thereof. The resorbable carrier is preferably made from a bioresorbable polymer. The bioresorbable polymer is preferably polyglycolide or polylactide, but may alternatively be made from any suitable bioresorbable material such as a biodegradable magnesium alloy or a corrodible iron alloy. If the bioresorbable polymer is polyglycolide (or any other material that absorbs into the body after approximately one month), the carrier absorbs into the body at about the same time the body heals around the implanted device, which may be advantageous in some situations. If the bioresorbable polymer is polylactide (or any other material that absorbs into the body after approximately one year), the carrier absorbs into the body much after the body heals around the implanted device, which may be advantageous in other situations.

The carrier 10 may further extend the functionality of the device by providing fluidic channels through which therapeutic drugs, drugs to inhibit biologic response to the implant, or any other suitable fluid or substance may be transmitted. The fluidic channels are preferably channels defined by the geometry of the carrier 10, but may alternatively be separate microtubes molded, inserted, woven, knitted, or otherwise disposed into the carrier 10. The channels preferably provide for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener (or even a shape-memory alloy such as Nitinol) may be inserted to aid with the implantation or to facilitate post-implantation navigation of the device. The shape of the carrier is preferably tubular with about a 1-mm diameter, but may alternatively be solid or any other suitable shape of any suitable diameter for the desired functions.

The carrier 10 is preferably made from a material that is woven or knitted, but may alternative be made from a material that is cast, molded, or machined. The carrier 10 is preferably flexible, but may alternatively be rigid or semi rigid. The material may be uniformly rigid, or rigid only in a particular direction (such as the axial direction). The resorbable carrier may also be impregnated with fluids and/or deliver the fluids such as drugs and/or neurotrophins, similar to the "Stent Device and Method" of U.S. Pat. No. 7,001,680, which is incorporated in its entirety by this reference. The carrier 10 may be further adapted to act as a template for tissue regeneration and/or as a matrix for autologous or analogous cells or stem cells.

The carrier 10 may be made from a combination of materials. The layers or portions of distinct materials may have distinct absorption, degradation, or incorporation times. The distinct materials may further include distinct particles, agents, and/or cells that they deliver or release into the tissue. The carrier 10 may further include scaffolding for structural support and/or for drug or cell delivery. The scaffolding is preferably bioresorbable, but may alternatively remain implanted with the device.

The carrier 10 may be manufactured in one of several variations. In a first variation, the carrier may be manufactured such that the weave of the material is large enough to accept "weaving" of the electrical subsystem 12 directly into the fabric. In this variation, the electrical subsystem can be adapted to be woven in and out of the resorbable carrier to secure the electrical subsystem 12 to the carrier 10. A single electrical subsystem 12 could be woven into the fabric or multiple subsystems could be incorporated, resulting in a three-dimensional system of electrical subsystems. In a second variation, the electrical subsystem could be coupled directly to the surface of the carrier using a biocompatible adhesive such as epoxy or silicone. In this variation, the weave of the resorbable carrier may be tighter and/or the porosity of the carrier may be smaller as the electrical subsystem 12 is not woven into the material in this variation. In a third variation, the resorbable carrier may be manufactured as a concentric, multi-lumen structure. In this variation, the electrical subsystem 12 may be coupled to the carrier between the inner and outer lumens of the electrical subsystem.

Although the carrier 10 is preferably one of these several variations, of several various materials, manufactured in several variations, the carrier may be any suitable element, material, manufactured in any suitable fashion to facilitate the insertion of the electrical subsystem 12 and to allow the electrical subsystem 12 to move freely in the tissue or other substances.

The electrical subsystem 12 of the preferred embodiments functions to interface with the tissue, or any other suitable substance, within which it has been implanted. The electrical subsystem 12 may include multiple different electrical subsystems or a plurality of the same subsystems. The electrical subsystem 12 is preferably at least one of several versions or any combination thereof.

The electrical subsystem 12 is preferably a neural interface electrode array. The electrode array preferably has a plurality of electrode sites, and more preferably both stimulation sites 20 and recording sites 22. The neural interface electrode array is adapted to provide dynamic tunable electrical stimulation ranging from stimulation with macroscale specificity to microscale directional, patterning. The electrode array is preferably adapted to optimally sample (record) and/or selectively activate (stimulate) neural populations. The plurality of electrode sites can be tuned for recording, stimulation, or any combination thereof. Additionally, at least two electrode sites may be grouped to form a larger composite site that enables tuning the neural interface region for recording and/or stimulation.

The neural interface electrode array is preferably made from a thin-film polymer substrate, such as parylene or some combination of parylene and inorganic dielectrics, but may alternatively be made out of any suitable material including, for example, silicon. The neural interface electrode array is preferably made such that there is high density of electrode sites at a first end of the array (the distal end) and bonding regions at a second end of the array (the proximal end). The distal end of the array is preferably coupled to the carrier 10 to provide structural support. The electrode array may further include fluidic channels providing the capability to deliver therapeutic drugs, drugs to inhibit biologic response to the implant, or any other suitable fluid.

The neural interface electrode array in this variation is preferably a composite assembly that includes the neural interface electrode array and the carrier 10. The neural interface electrode array includes two pieces, a distal element and a proximal element. The distal element wraps or is woven around the circumference of the carrier 10. Ascending from the distal element, are preferably interconnects that transition from the outer surface of the carrier 10 into a single connector 14, such that the entire proximal element is imbedded in silicone. To facilitate adhesion between the carrier 10 and the neural interface electrode array, small non-homogeneous perforations are preferably micromachined in the neural interface electrode array to allow for the material of the carrier 10 to form a robust anchor with the electrode array.

Figure 3:
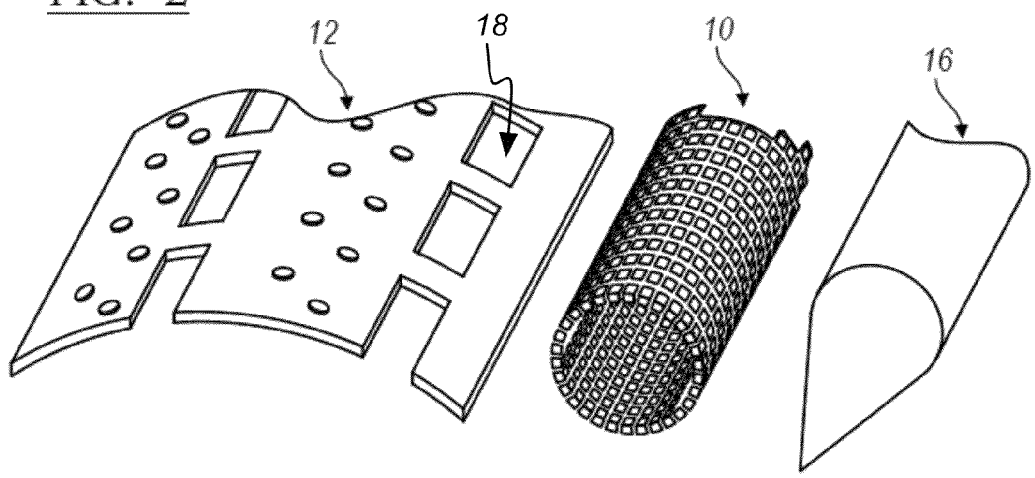
FIG. 3 is a representation of the device of a second version of the preferred embodiments of the invention, shown in an exploded, pre-assembled view.

In a second version of the preferred embodiments, as shown in FIG. 3, the neural interface electrode array preferably defines series of "cut-aways" or perforations 18 that axially extend in a discontinuous manner along the length of the neural interface electrode array. With the perforations, the neural interface electrode array preferably has adequate flexibility to allow bending and flowing of the device within body tissue after implantation of the device. The perforations 18 preferably extend in a radial direction completely through the neural interface electrode array, and preferably extend in a circumferential direction approximately 45-90 degrees. The neural interface electrode array preferably includes two perforation series, and thus the neural interface electrode array preferably extends 180-270 degrees in the areas with perforations. The perforation series is preferably discontinuous (i.e., the neural interface electrode array extends completely in the circumferential direction at particular points along the length of the neural interface electrode array). While the neural interface electrode array has been described as having perforations, it is also possible for the neural interface electrode array to be described as being one or more strips that are circumferentially connected by several "bridges".

In a third version of the preferred embodiments, the neural interface electrode array omits the "bridges" and is merely one or more rectangular and generally planar (i.e., either flat or slightly curved) "strips". The carrier provides structural support for these "strips" to be placed onto a stylet and implanted into body tissue. Although the electrical subsystem 12 is preferably one of these three versions, the electrical subsystem 12 may be any suitable element or combination of elements to perform the desired functions.

The device of the preferred embodiments may further include an additional electrical subsystem that functions to operate with the electrical subsystem 12. The additional electrical subsystem may include multiple different electrical subsystems or a plurality of the same subsystems. The additional electrical subsystem is preferably at least one of several versions or any combination thereof. In a first version, the additional electrical subsystem is a suitable electronic subsystem to operate with an implantable neural interface. The additional electrical subsystem may be a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable pulse generator, an implantable rechargeable battery, integrated electronics for either real-time signal processing of the input (recorded) or output (stimulation) signals, integrated electronics for control of the fluidic components, any other suitable electrical subsystem, or any combination thereof. Although the additional electrical subsystem is preferably one of these several subsystems, the additional electrical subsystem may be any suitable element or combination of elements to operate any suitable electrical subsystem 12.

The device of the preferred embodiments may further include a connector 14 that functions to couple the electrical subsystem 12 to the additional electrical subsystem. The connector 14 is preferably one of several versions. As shown in FIGS. 1 and 2, the cable is preferably a flexible ribbon cable. The ribbon cable is preferably polymer ribbon cable, but may alternatively be any other suitable ribbon cable. The connector 14 may alternatively be any suitable element to couple the electrical subsystem 12 to the additional electrical subsystem, such as wires, conductive interconnects, etc. The ribbon cable may be encased in silicone or any other suitable material. In some versions, the electrical subsystem may have multiple ribbon cables. Preferably, multiple ribbon cables would be physically attached along their entire length, using a suitable adhesive such as medical grade adhesive or any other suitable connection mechanism. The cable is preferably connected to the electrical subsystems through ball bonds or any other suitable connection mechanisms. The connector 14 may alternatively be seamlessly manufactured with the first and or additional electrical subsystem. The connector 14 may further include fluidic channels adapted to deliver therapeutic drugs, drugs to inhibit biologic response to the implant, or any other suitable fluid.

As shown in FIG. 3, the device of the preferred embodiments may further include a stylet 16. The stylet 16 of the preferred embodiments functions to penetrate the tissue or other material and/or functions to provide structural support to the device during implantation of the device. The stylet 16 is preferably inserted into a lumen of the carrier 10, but may alternatively be located and inserted into any suitable component of the device in any suitable manner. The stylet 16 may include a sharpened end adapted to penetrate the tissue and aid in the insertion of the stylet, the carrier 10, and/or the electrical subsystems into the tissue. The stylet 16 is preferably removed from the tissue following the placement of an electrical subsystem, but may alternatively be adapted to remain in the tissue while still allowing the implanted electrical subsystem 12 to float freely in the brain. This may be accomplished by the stylet being selectively flexible (through electrical stimulus or other suitable method) or by being resorbable into the tissue after a period of time. The stylet 16 is preferably made from a stiff material such as metal, but may alternatively be made from any suitable material. In one variation, the metal is an insulated metal wire. In this variation, the insulated metal wire may not have insulation covering a sharpened tip, and thus can be used as a conventional single-channel microelectrode.

Figure 4A:
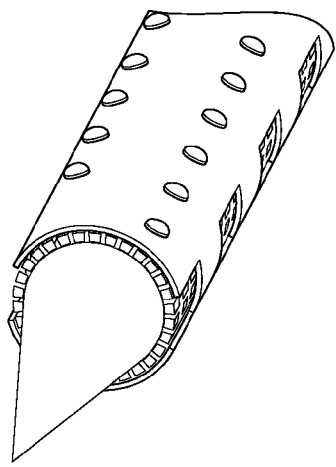
FIGS. 4A-C are representations of the method of the preferred embodiments of the invention, shown with the three major steps.
Figure 4B:
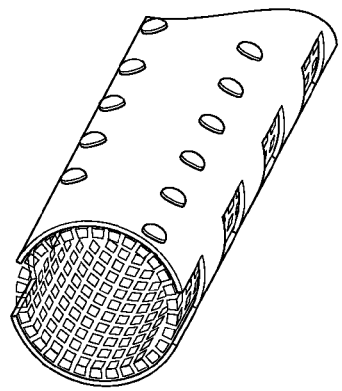
Figure 4C:
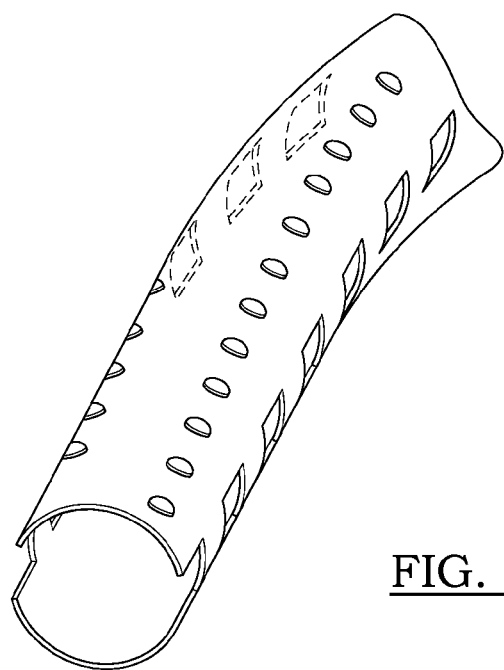

As shown in FIG. 4, a method of implanting and using the implantable device and its corresponding electrical components preferably includes the following steps: (a) providing an electrical subsystem and a carrier that provides structural support for the electrical subsystem; (b) implanting the electrical subsystem and the carrier into the body tissue; and (c) dissolving the carrier into the body tissue and allowing the electrical subsystem to flex within and interface with the body tissue. Step (c) may include dissolving the carrier into the body tissue at a rate approximately equal to the healing process of the body tissue, or may include dissolving the carrier into the body tissue at a rate much slower than the healing process of the body tissue. The method may also include providing a stylet, placing the electrical subsystem and the carrier onto the stylet, and penetrating the body tissue with the stylet.

Although omitted for conciseness, the preferred embodiments include every combination and permutation of the various carriers 10, the various electrical subsystems, the various connectors, the various stylets, and the various methods of use.

As a person skilled in the art will recognize from the previous detailed description and from the figures and claims, modifications and changes can be made to the preferred embodiments of the invention without departing from the scope of this invention defined in the following claim.

I claim:

1. An implantable electrode device, comprising:
   a) a carrier extending along a first carrier length from a proximal carrier portion to a distal carrier portion having a distal carrier end;
   b) a first electrical subsystem, comprising:
      i) at least one electrode site;
      ii) an electrode substrate supporting the at least one electrode site, wherein at least a portion of the electrode substrate supporting the at least one electrode site is woven with the carrier so that the at least one electrode site has an exposed surface facing outwardly from the electrode substrate opposite the carrier; and
      iii) an electrical connector extending from the at least one electrode site to a proximal connector portion adjacent to the proximal carrier portion; and
   c) wherein the carrier is of a bioresorbable material that is absorbable into body tissue after implantation of the electrode device comprising the carrier and the first electrical subsystem, thereby leaving the at least one electrode site facing outwardly toward the body tissue from the supporting electrode substrate.

2. The implantable electrode device of claim 1, wherein the first electrical subsystem is flexible after absorption of the carrier into body tissue.

3. The implantable electrode device of claim 1 wherein the bioresorbable material of the carrier is selected from the group consisting of polyglycolide, polylactide, a magnesium alloy, and a corrodible iron alloy.

4. The implantable electrode device of claim 1, wherein the carrier has a tubular shape.

5. The implantable electrode device of claim 4 wherein there are a plurality of electrode sites supported by the electrode substrate and wherein the electrode substrate is woven with the tubular carrier so that the plurality of electrode sites extend both circumferentially and axially relative to the first carrier length.

6. The implantable electrode device of claim 4 wherein the tubular carrier has a diameter of about one millimeter.

7. The implantable electrode device of claim 1 wherein the carrier has a woven structure.

8. The implantable electrode device of claim 1, wherein the at least one electrode site of the first electrical subsystem is configured to interface with neural tissue.

9. The implantable electrode device of claim 8, wherein the first electrical subsystem includes a plurality of electrode sites that are configured to electrically stimulate different portions of neural tissue.

10. The implantable electrode device of claim 1 wherein there are a plurality of electrode sites supported by the electrode substrate and wherein the electrode substrate is woven with the carrier so that the plurality of electrode sites extend both circumferentially and axially relative to the first carrier length.

11. The implantable electrode device of claim 1 wherein there are a plurality of electrode sites supported by the electrode substrate, and wherein the plurality of electrode sites are configured to electrically record different portions of neural tissue.

12. The implantable electrode device of claim 1 wherein the electrode substrate is of a thin-film polymer.

13. The implantable electrode device of claim 12, wherein the thin-film polymer is selected from the group consisting of parylene and silicone.

14. The implantable electrode device of claim 1, wherein the electrode substrate has a tubular shape.

15. The implantable electrode device of claim 1 wherein the electrode substrate has a series of perforations that axially extend in a discontinuous manner along a second electrode substrate length.

16. The implantable electrode device of claim 1 wherein the electrode substrate is a thin-film substrate.

17. The implantable electrode device of claim 1 wherein the first electrical subsystem has an elongated, substantially planar shape.

18. The implantable electrode device of claim 1 wherein the proximal connector portion of the first electrical subsystem is electrically connectable to a second electrical subsystem that is configured to control the at least one electrode site.

19. The implantable electrode device of claim 1 wherein the electrical connector is a flexible ribbon cable.

20. The implantable electrode device of claim 1 wherein a lumen extends through the carrier along the first carrier length from the proximal carrier portion to the distal carrier end.

21. The implantable electrode device of claim 20 wherein the lumen is configured to receive a stylet having a sharpened end adapted to extend outwardly from the distal carrier end.

22. The implantable electrode device of claim 1 wherein the electrode substrate includes longitudinal and circumferential bridge strips, and wherein one or more longitudinal bridge strip is connected by the circumferential bridge strips, thereby defining a series of discontinuous perforations in the electrode substrate of the first electrical subsystem.

23. The implantable electrode device of claim 1 wherein the carrier comprises an inner tubular sidewall disposed inside an outer tubular sidewall with the first electrical subsystem located between the inner and outer carrier sidewalls, but with the exposed surface of the at least one electrode site facing outwardly from the electrode substrate opposite the inner and outer carrier sidewalls.

24. The implantable electrode device of claim 1 wherein the bioresorhable material of the carrier is completely absorbable into body tissue within about one month after implantation of the electrode device.

25. The implantable electrode device of claim 1 wherein the bioresorhable material of the carrier is completely absorbable into body tissue within about one year after implantation of the electrode device.

26. The implantable electrode device of claim 1 wherein the first electrical subsystem defines a perforation, and wherein the carrier is anchorable in body tissue in the perforation.

27. An implantable electrode device, comprising:
a) a carrier extending along a first carrier length from a proximal carrier portion to a distal carrier portion;
b) an electrical subsystem, comprising:
   i) a plurality of electrode sites;
   ii) an electrode substrate supporting the plurality of electrode sites, wherein at least a portion of the electrode substrate supporting the plurality of electrode sites is woven with the carrier so that the electrode sites are both circumferentially and axially disposed relative to the first carrier length and wherein the plurality of electrode sites have respective exposed surfaces facing outwardly from the electrode substrate opposite the carrier; and
   iii) an electrical connector extending from each of the plurality of electrode sites to a proximal connector portion adjacent to the proximal carrier portion; and
c) wherein the carrier is of a bioresorbable polymer selected from the group consisting of polyglycolide, polylactide, a magnesium alloy, and a corrodible iron alloy and that is absorbable into body tissue after implantation of the electrode device comprising the carrier and the electrical subsystem, thereby leaving the plurality of electrode sites facing outwardly toward the body tissue from the supporting electrode substrate.

28. The implantable electrode device of claim 27 wherein the carrier has a tubular shape.

29. The implantable electrode device of claim 27 wherein a lumen extends through the carrier along the first carrier length from the proximal carrier portion to a distal carrier end of the distal carrier portion.

30. The implantable electrode device of claim 27 wherein the electrode substrate has a tubular shape.

31. The implantable electrode device of claim 27 wherein the electrode substrate is substantially planar.

32. An implantable electrode device, comprising:
a) a carrier, comprising:
   i) a woven carrier sidewall extending along a first carrier length from a proximal carrier portion to a distal carrier portion having a distal carrier end; and
   ii) a lumen extending through the carrier along the first carrier length from the proximal carrier portion to the distal carrier end;
b) an electrical subsystem, comprising:
   i) at least one electrode site;
   ii) an electrode substrate supporting the electrode site, wherein at least a portion of the electrode substrate supporting the at least one electrode site is interwoven with the carrier sidewall so that the at least one electrode site has an exposed electrode surface facing outwardly, away from the electrode substrate interwoven with the carrier; and
   iii) an electrical connector extending from the at least one electrode site to a proximal connector portion adjacent to the proximal carrier portion; and
c) wherein the carrier sidewall is of a bioresorbable polymer that is absorbable into body tissue after implantation of the electrode device comprising the carrier interwoven with the electrode substrate, thereby leaving the at least one electrode site facing outwardly, away from the supporting electrode substrate.

33. The implantable electrode device of claim 32 wherein the carrier sidewall has a tubular shape.

34. The implantable electrode device of claim 32 wherein the electrode substrate has a tubular shape.

35. The implantable electrode device of claim 32 wherein the electrical subsystem has an elongated, substantially planar shape.

36. An implantable electrode device, comprising:
a) a carrier comprising a carrier sidewall extending along a carrier length from a proximal carrier portion to a distal carrier portion having a distal carrier end;
b) an electrical subsystem, comprising:
  i) a plurality of electrode sites;
  ii) an electrode substrate supporting the plurality of electrode sites, wherein the electrode substrate is supported by the carrier with the plurality of electrode sites extending both circumferentially and axially relative to the carrier length and wherein the electrode sites each have an exposed surface facing outwardly from the electrode substrate opposite the carrier; and
  iii) an electrical connector extending from each of the plurality of electrode sites to a proximal connector portion adjacent to the proximal carrier portion; and
c) wherein the carrier is of a bioresorbable material that is absorbable into body tissue after implantation of the electrode device comprising the carrier and the electrical subsystem, thereby leaving the plurality electrode sites facing outwardly toward the body tissue from the supporting electrode substrate.

37. The implantable electrode device of claim 36, wherein the electrode substrate has a tubular shape.

38. An implantable electrode device, comprising:
a) a carrier, comprising:
  i) a carrier sidewall extending along a carrier length from a proximal carrier portion to a distal carrier portion having a distal carrier end; and
  ii) a lumen extending through the carrier along the carrier length from the proximal carrier portion to the distal carrier end;
b) an electrical subsystem, comprising:
  i) at least one electrode site;
  ii) an electrode substrate supporting the at least one electrode site, wherein at least a portion of the electrode substrate supporting the at least one electrode site is supported by the carrier so that the at least one electrode site has an exposed surface facing outwardly from the electrode substrate opposite the carrier; and
  iii) an electrical connector extending from the at least one electrode site to a proximal connector portion adjacent to the proximal carrier portion; and
c) wherein the carrier is of a bioresorbable material that is absorbable into body tissue after implantation of the electrode device comprising the carrier and the electrical subsystem, thereby leaving the at least one electrode site facing outwardly toward the body tissue from the supporting electrode substrate.

39. The implantable electrode device of claim 38 wherein the carrier sidewall has a substantially tubular shape.

* * * * *